(12) United States Patent
Weaver, II et al.

(10) Patent No.: US 7,229,426 B2
(45) Date of Patent: Jun. 12, 2007

(54) TENNIS ELBOW SUPPORT COMPRISING TENDON PAD

(75) Inventors: Edward Leonard Weaver, II, Milford, OH (US); Richard Gregory Taylor, Cincinnati, OH (US)

(73) Assignee: Beiersdorf, Inc., Wilton, CT (US)

( * ) Notice: Subject to any disclaimer, the term of this patent is extended or adjusted under 35 U.S.C. 154(b) by 0 days.

(21) Appl. No.: 11/340,360

(22) Filed: Jan. 26, 2006

(65) Prior Publication Data

US 2006/0122549 A1 Jun. 8, 2006

Related U.S. Application Data

(60) Division of application No. 10/842,944, filed on May 10, 2004, now Pat. No. 7,172,566, which is a continuation of application No. 10/213,224, filed on Aug. 6, 2002, now Pat. No. 6,755,800.

(60) Provisional application No. 60/310,751, filed on Aug. 8, 2001.

(51) Int. Cl.
*A61F 5/00* (2006.01)
*A61F 13/00* (2006.01)

(52) U.S. Cl. .................. 602/20; 602/62; 128/112.1

(58) Field of Classification Search ............ 2/311–312; 602/20, 23, 60, 61, 62; 128/112.1
See application file for complete search history.

(56) References Cited

U.S. PATENT DOCUMENTS

| 1,697,833 | A | 1/1929 | Lane |
| 1,925,615 | A | 9/1933 | Stuart |
| 2,271,927 | A | 2/1942 | Saighman |
| 3,970,081 | A | 7/1976 | Applegate, Jr. |
| 4,136,686 | A | 1/1979 | Arluck |
| 4,182,318 | A | 1/1980 | Beige et al. |
| 4,243,028 | A | 1/1981 | Puyana |
| 4,246,658 | A | 1/1981 | Liaw |
| 4,292,263 | A | 9/1981 | Hanrahan et al. |
| 4,308,861 | A | 1/1982 | Kelly |
| 4,334,528 | A | 6/1982 | Gauvry |
| D272,186 | S | 1/1984 | Peck |
| 4,441,493 | A | 4/1984 | Nirschl |
| 4,628,918 | A | 12/1986 | Johnson, Jr. |
| 4,821,708 | A | 4/1989 | Guignard et al. |
| 4,832,010 | A | 5/1989 | Lerman |
| D308,465 | S | 6/1990 | Hietter |
| 4,991,573 | A | 2/1991 | Miller |

(Continued)

FOREIGN PATENT DOCUMENTS

EP  0 454 402 A2  10/1991

*Primary Examiner*—Kim M. Lewis
(74) *Attorney, Agent, or Firm*—Alston & Bird LLP

(57) ABSTRACT

A tennis elbow support comprising a main body having an opening and a tendon pad having a pad base and a raised portion that projects from the pad base. The tendon pad is inserted into the opening so that the raised portion projects outwardly from a bottom surface of the main body. The main body can be releasably secured in a substantially circular configuration so that the support can be placed around the forearm of a user and the tennis elbow support can be tightened around the arm of the user with tendon pad in contact with the arm so that straight-line pressure is applied across the extensor muscle and tendon.

15 Claims, 4 Drawing Sheets

U.S. PATENT DOCUMENTS

| | | |
|---|---|---|
| 5,010,902 A | 4/1991 | Rambo et al. |
| 5,063,913 A | 11/1991 | Nyi |
| 5,078,728 A | 1/1992 | Giarratano |
| 5,152,302 A | 10/1992 | Fareed |
| 5,154,690 A | 10/1992 | Shiono |
| 5,165,402 A | 11/1992 | McCoy |
| 5,234,459 A | 8/1993 | Lee |
| 5,295,951 A | 3/1994 | Fareed |
| 5,306,229 A | 4/1994 | Brandt et al. |
| 5,312,350 A | 5/1994 | Jacobs |
| 5,334,135 A | 8/1994 | Grim et al. |
| 5,338,290 A | 8/1994 | Aboud |
| 5,372,575 A | 12/1994 | Sebastian |
| D356,433 S | 3/1995 | Humphrey |
| 5,419,757 A | 5/1995 | Daneshvar |
| 5,429,587 A | 7/1995 | Gates |
| 5,441,058 A | 8/1995 | Fareed |
| D368,331 S | 3/1996 | Chiang |
| D368,332 S | 3/1996 | Chiang |
| D368,351 S | 4/1996 | Yewer, Jr. |
| 5,512,056 A | 4/1996 | Stevens et al. |
| D369,866 S | 5/1996 | Baughn |
| 5,613,941 A | 3/1997 | Prengler |
| 5,624,388 A | 4/1997 | Lehr |
| D381,427 S | 7/1997 | Marrero |
| 5,642,525 A | 7/1997 | Ketola |
| 5,642,739 A | 7/1997 | Fareed |
| 5,647,062 A | 7/1997 | Nigbur |
| 5,695,452 A | 12/1997 | Grim et al. |
| 5,695,520 A | 12/1997 | Bruckner et al. |
| 5,711,029 A | 1/1998 | Visco et al. |
| 5,743,806 A | 4/1998 | Brennan |
| 5,782,743 A | 7/1998 | Russell |
| 5,792,176 A | 8/1998 | Chang |
| 5,819,313 A | 10/1998 | McCrane |
| 5,865,775 A | 2/1999 | Peoples et al. |
| 5,891,079 A | 4/1999 | Barnes |
| 5,915,535 A | 6/1999 | Henrekin-Jordan |
| 5,921,949 A | 7/1999 | Dray |
| 5,971,947 A | 10/1999 | McNally et al. |
| 6,007,503 A | 12/1999 | Berger et al. |
| 6,007,508 A | 12/1999 | Reinhardt et al. |
| 6,077,241 A | 6/2000 | Fareed |
| 6,093,143 A | 7/2000 | Nagler |
| 6,120,472 A | 9/2000 | Singer, Jr. |
| 6,129,694 A | 10/2000 | Bodenschatz |
| 6,149,616 A | 11/2000 | Szlema et al. |
| 6,149,617 A | 11/2000 | McNally et al. |
| 6,149,618 A | 11/2000 | Sato |
| 6,152,893 A | 11/2000 | Pigg et al. |
| 6,155,999 A | 12/2000 | Bartlett |
| 6,200,286 B1 | 3/2001 | Zamani |
| 6,217,536 B1 | 4/2001 | Gustafson |
| 6,224,564 B1 | 5/2001 | Korobow |
| 6,240,566 B1 | 6/2001 | Scantlin |
| 6,254,554 B1 | 7/2001 | Turtzo |
| 6,254,613 B1 | 7/2001 | Harrison |
| D455,213 S | 4/2002 | Weaver, II et al. |
| 6,398,749 B1 | 6/2002 | Slautterback |
| 6,478,760 B2 | 11/2002 | Darcey |

US 7,229,426 B2

TENNIS ELBOW SUPPORT COMPRISING TENDON PAD

CROSS-REFERENCE TO RELATED APPLICATIONS

This application is a divisional of application Ser. No. 10/842,944, which was filed May 10, 2004, now U.S. Pat. No. 7,172,566, which is a continuation of application Ser. No. 10/213,224, which was filed Aug. 6, 2002 now U.S. Pat. No. 6,755,800 and entitled "Tennis Elbow Support Comprising Tendon Pad", and which claims the benefit of Provisional Application 60/310,751, filed Aug. 8, 2001. The present application claims priority from all above-referenced applications and hereby incorporates application Ser. No. 10/842,944 by reference.

BACKGROUND OF THE INVENTION

The invention pertains to a tennis elbow support comprising a tendon pad having a raised portion, and optionally, a protrusion that projects substantially about the center from the raised portion. The invention provides relief to the user for the pain and discomfort associated with Lateral Epicondylitis and other injuries to the arm and joints of a user.

SUMMARY OF THE INVENTION

The tennis elbow support is generally in the shape of a strap having a main body, a tendon pad, a top cover assembly comprising securing means and a hook tab. The hook tab can be releasably fastened to an upper surface of the main body and/or the securing means of the top cover assembly in a manner such that the tennis elbow support can be shaped into a substantially circular form and slipped on to an appendage of a user, generally the forearm, with the tendon pad in contact with the outside of the user's forearm.

The tendon pad may be secured to the main body of the tennis elbow support through an opening in the main body so that the base of the tendon pad is flush with the main body, or the tendon pad may be secured to the top cover assembly and inserted through the opening of the main body. The tendon pad has a raised portion which may comprise a protrusion in about the center of the raised portion. The tendon pad offers perpendicular, straight-line pressure (compression) both localized and distributed across the extensor muscle and tendon, and the protrusion applies focused pressure against the tendon.

DETAILED DESCRIPTION OF THE INVENTION

Figure 1:
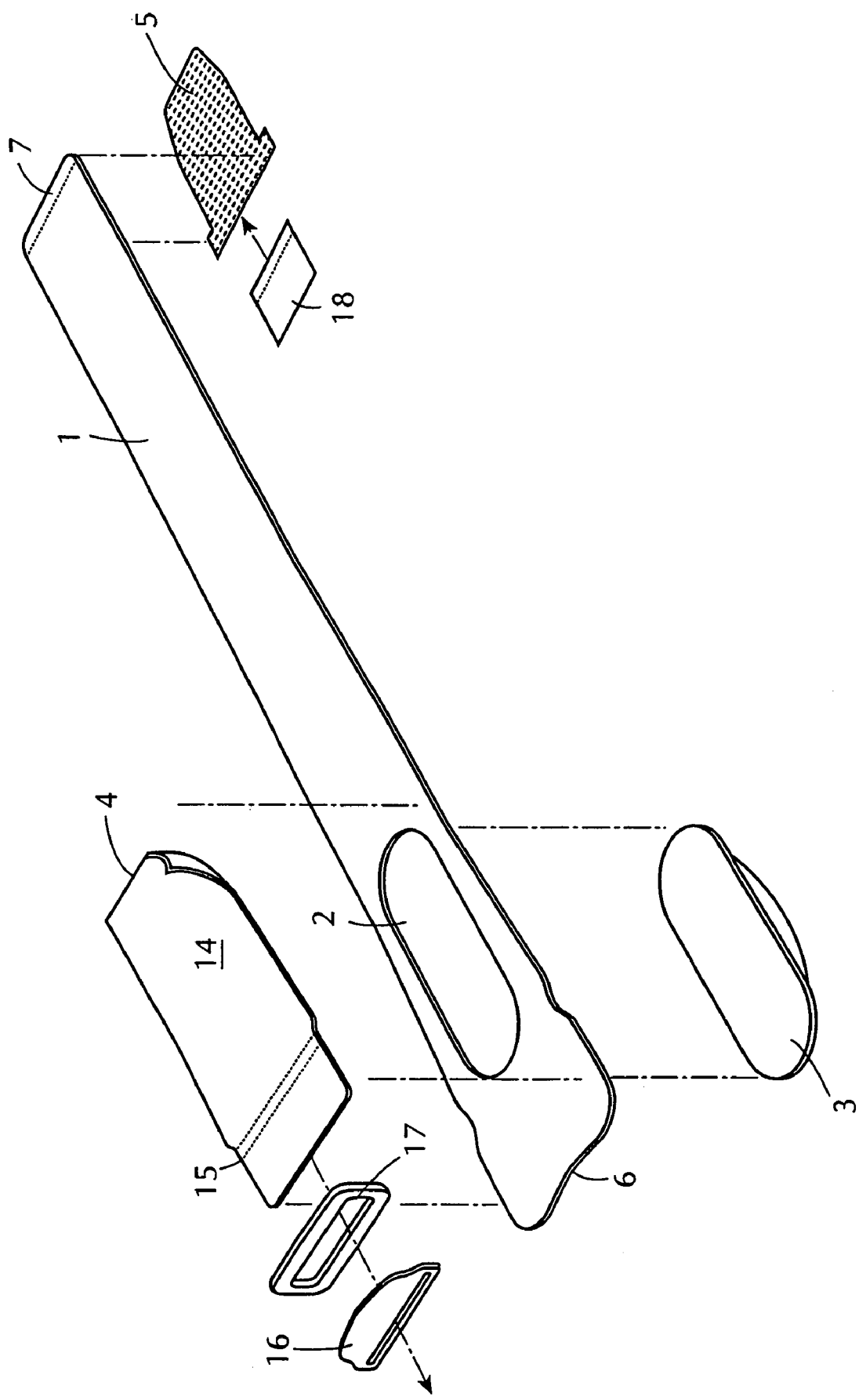
FIG. 1 is an assembly view of a tennis elbow support in accordance with an embodiment of the invention.

Referring to FIG. 1, the tennis elbow support comprises a main body 1 having an opening 2 for the tendon pad 3. The tennis elbow support further comprises a top cover assembly 4 and a hook tab 5. The main body has an enlarged end 6 approximate to the opening 2, and a second end 7.

Figure 2:
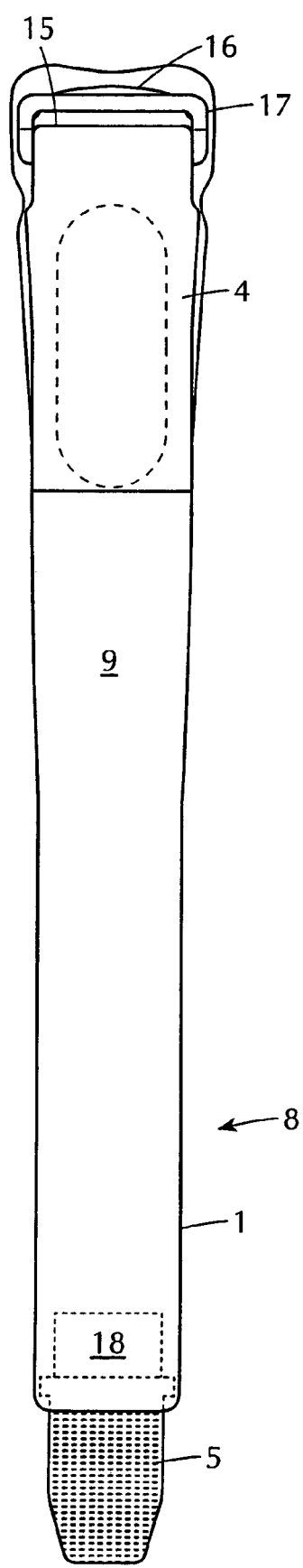
FIG. 2 is a top view of a tennis elbow support in accordance with an embodiment of the invention.
Figure 3:
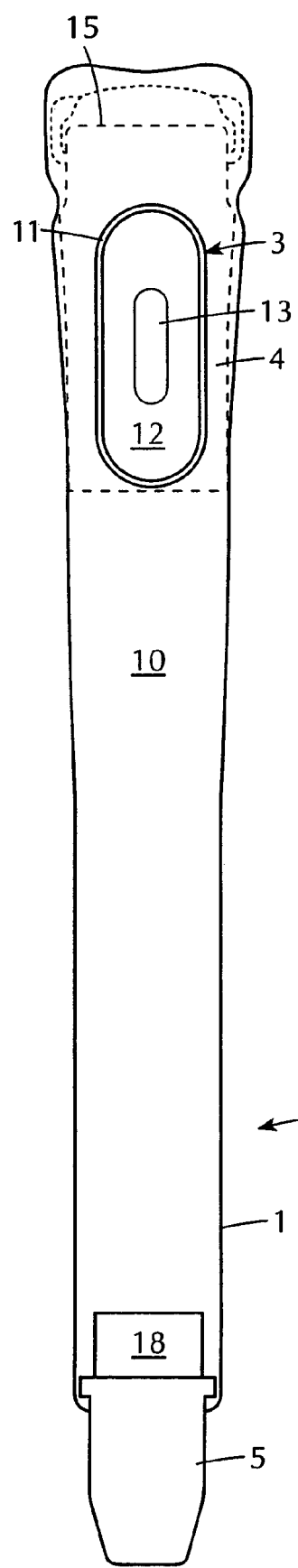
FIG. 3 is a bottom view of a tennis elbow support in accordance with an embodiment of the invention.

The assembled tennis elbow support 8 is shown generally in FIGS. 2 and 3 with respect to embodiments wherein the tendon pad 3 is generally oval in shape. As shown in FIGS. 2 and 3, the main body 1 has an upper surface 9 and a bottom surface 10. The main body 1, may be made from any non-stretch material, which may be a moisture wicking material. Preferably, the main body is a laminate comprising all or part of a releasable fastener, most preferably having the upper surface 9, e.g. the exposed side of the laminate when the support is wrapped around the user's arm, made from material that is hook engagable for full-length adjustability. Examples of laminates that may be used for the main body are VELCRO® laminate (or equal): LP3610-0698/ 0.125 G45 (Char.)/ORTHOWICK® (Black) or LP3610-0698 (Black)/0.125" G45L (Black)/Tricot (Black) with zero stretch available from Velcro USA Inc., Manchester, N.H., USA. The Orthowick or tricot side of the laminate forms the bottom surface 10 of the main body and is worn against the skin when the support is wrapped around the user's arm for a low skin irritation and soft feel.

Figure 4:
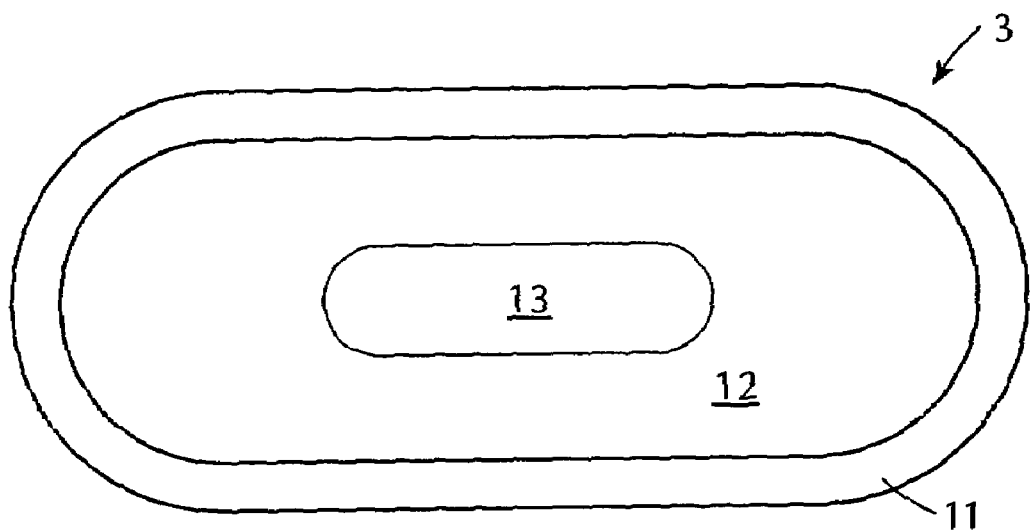
FIG. 4 is a top view of a tendon pad in accordance with an embodiment of the invention.
Figure 5:
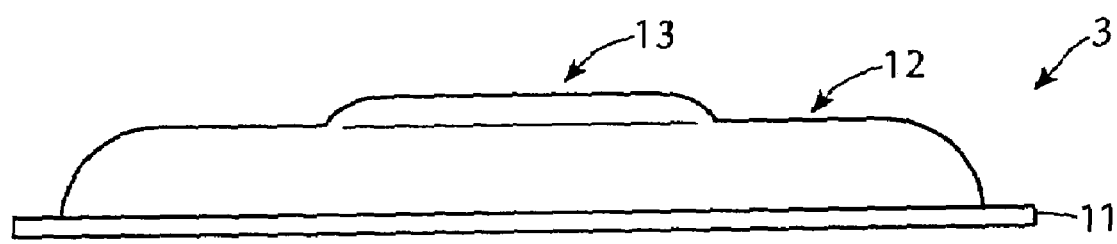
FIG. 5 is a side view of a tendon pad in accordance with an embodiment of the invention.

The tendon pad 3, as shown in FIGS. 4 and 5 with respect to an embodiment of the invention wherein the tendon pad 3 is generally oval in shape, comprises a pad base 11 and a raised portion 12 which projects from the pad base 11 and, optionally, a protrusion 13 which projects substantially about the center from the raised portion 12. Although, FIGS. 1–5 show the pad base 11, raised portion 12 and protrusion 13 substantially in the shape of an oval, these elements of the tendon pad 3 may be configured in any geometrical shape or combination of geometrical shapes, such as circular, square, rectangular, triangular, trapezoidal and the like, or combinations thereof, with the opening 2 of the main body 1 having a shape corresponding to that of the pad base 11 without deviating from the scope of the invention. The design of the raised portion 12 offers a perpendicular, straight-line pressure (compression) both localized and distributed across the extensor muscle and tendon. The configuration of the protrusion projecting substantially about the center from the raised portion 12 provides for the protrusion 13 to apply a focused pressure against the tendon.

The pad base 11 is generally made from a semi-rigid or non-stretch material with the raised portion 12 and protrusion 13 formed from soft compressible material such as foam. In addition to foam, the raised portion 12 and protrusion 13 may be made from other compressible material such as gel, thin or viscous liquid, gas, particulate and the like or combinations of materials. The compressible material may be covered by textile material that is secured to the pad base 11 by first attachment means, such as Radio Frequency welding (RF Welding), stitching, adhesives, and the like, and combinations thereof.

As shown in FIGS. 1–3, the tendon pad 3 is located at the main body 1 in the area of the opening 2. The opening 2 may be located at any point of the main body 1, but as show in FIGS. 1–3, the opening 2 is preferably approximate to the enlarged end 6 so that the tendon pad is oriented with the extensor muscle and tendon when worn by a user. The opening 2 is configured to accept the pad base 11 such that the raised portion 12 and optional protrusion 13 project outwardly from the bottom surface 10 of the main body 1. The pad base 11 has a thickness substantially the same as the thickness of the main body 1 such that when the tendon pad 3 is inserted into the opening 2, the pad base 11 may be preferably substantially flush, more preferably flush, with the bottom surface 10 which minimizes or eliminates potential harsh edges of the tendon pad 3 rubbing against skin of a user and provides for enhanced comfort. In an embodiment of the invention, however, the bottom surface 10 may completely or partially overlap the pad base 11 which also minimizes or eliminates potential harsh edges of the tendon pad 3 rubbing against skin of a user and provides for enhanced comfort. The tendon pad 3 may be secured to the main body 1 by a second attachment means, such as RF Welding, stitching, adhesives, and the like, and combinations thereof, however, as discussed below, the tendon pad may preferably be secured to the top cover assembly. Welding attachment means, such as RF Welding, eliminates stitching at the point where the tendon pad 3 is secured to the main body 1 which enhances comfort when the tennis elbow support is worn.

Although FIGS. 1–3 show a top cover assembly having one buckle loop 17, it is understood that the tennis elbow support may comprise one or more buckle loops 17 and also one or more buckle protectors 16. As shown in FIG. 1, the top cover assembly 4 comprises a substantially rectangular textile material piece 14 having a tapered end 15, a buckle protector 16 generally made from rigid material and a buckle loop 17 generally made from rigid material. The buckle protector 16 may be in any shape, but is preferably substantially a modified trapezoid with curved tapered sides, and the buckle loop 17 may be of any shape having an opening about its center, but is preferably substantially a rectangle with a corresponding substantially rectangular opening defined by contiguous inner walls of the rectangular piece about the center of the buckle loop 17. The textile material piece 14 may be made from VELCRO® woven nylon loop or the like.

As shown in FIGS. 2 and 3, the tapered end 15 is folded over itself and arranged in a loop orientation with the buckle protector 16 and buckle loop 17 within the inner opening defined by the loop of the tapered end 15. The tapered end 15 is secured upon itself in loop orientation by top cover attachment means, such as RF Welding, ultrasonic attachment means, other types of welding, stitching, adhesives, and the like, and combinations thereof. For example, the inner surface of the loop may comprise adhesive, such as urethane adhesive or the like, which is activated by radio wave frequency during an RF Welding process. The buckle protector 16 assists the user in avoiding an excessive amount of material of the main body from being pulled into the buckle loop 17 when the user releasably secures the tennis elbow support to the arm.

As shown in FIGS. 1–3, the top cover assembly 4 is attached to the upper surface 9 of the main body 1 in about the area of the enlarged end 6. The top cover assembly 4 is secured to the upper surface 9 of the main body 1 such that the textile material piece 14 does not extend substantially, if at all, beyond the main body 1. The top cover assembly is secured to the main body by a third attachment means, such as RF Welding, stitching, adhesives, and the like, and combinations thereof.

Referring again to FIGS. 1–3, in a preferred embodiment of the invention the tendon pad 3 is secured to the top cover assembly 4 by tendon pad attachment means such as RF Welding, stitching, adhesives and the like. The top cover assembly 4 with the tendon pad 3 located at the opening 2 is secured to the main body 1 by the third attachment means such that the upper surface 9 of the pad base 11 and the raised portion 12 and optional protrusion 13 projects from the bottom surface 10 of the main body 1. In this embodiment, the bottom surface 10 may partially or completely overlap the pad base 11. The tendon pad 3 may be secured to the top cover assembly 4 at the same time the top cover assembly is secured to the main body 1.

The hook tab 5 comprises one or more pieces of textile material with a fastening system and, preferably, one or more brand labels. As shown in FIGS. 1–3, the hook tab 5 is secured to the main body 1 at the second end 7 such that at least a portion of the hook tab extends substantially planar from the second end 7. FIGS. 1–3 show an embodiment wherein the hook tab 5 comprises a piece of textile material which is generally non-stretchable and has a releasable fastener, preferably the hook portion of a hook and loop type fastener on at least the side that extends from the upper surface of the main body. The hook tab is preferably secured to the bottom surface 10 of the main body 1 by fourth attachment means, such as RF Welding, stitching, adhesives, and the like, and combinations thereof. In addition, a brand label 18 may be secured at the second end 7 of the main body 1 between the hook tab 5 and the bottom surface 10 of the main body 1 at any point about the location where the main body 1 and hook tab 5 are secured, preferably about the center of the point of attachment, such that the brand label projects about substantially parallel to the main body 1 and extends planar from the hook tab 5. The brand label 18 refers to a piece of material, such as textile material, which may include information about the product and manufacturer. The brand label 18 helps to hold the end of the main body 1 within the rigid loop 17 when user is not wearing the tennis elbow support so that the tennis elbow support maintains a substantially circular shape when not in use allowing for quicker application and reapplication by the user and easier use.

Figure 6:
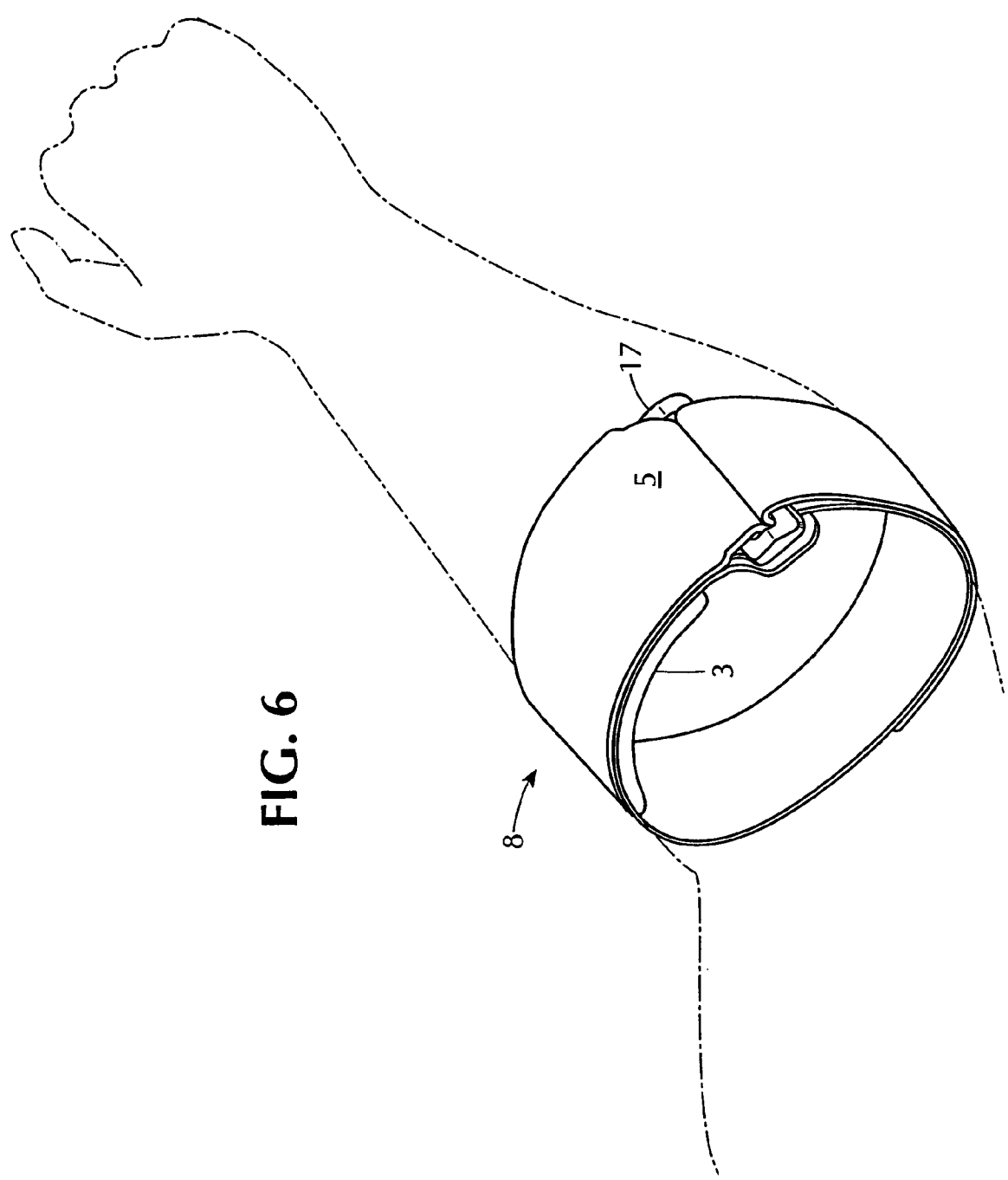
FIG. 6 is a perspective view of the tennis elbow support on the forearm of a user.

As shown in FIG. 6, the tennis elbow support 8 is worn on the user's arm such that the tendon pad 3 is in contact with the outside of a user's arm so that straight-line pressure is applied across the extensor muscle and tendon. The tennis elbow support can be formed into a substantially circular shape by inserting the hook tab 5 through the buckle loop 17 and overlapping part of the upper surface of the main body against itself. The user then inserts the arm through the substantially circular shaped tennis elbow support with the tendon pad properly positioned, and tightens as needed to accommodate the arm by overlapping the main body 1 against itself through the buckle loop 17. The hook portion of the hook and loop type fastener of the hook tab 5 is then releasably secured to the hook engageable portion, e.g. loop portion, of the upper surface 9 of the main body, and/or the textile material piece 14 of the top cover assembly 4. The circular configuration is maintained by the brand label resistance to go through the buckle loop 17 in a backward direction. It should be understood to one skilled in the art that although the means forming a substantially circular shape and securing the tennis elbow support around the arm of a user is described with respect to hook and loop type fasteners, any type of fastening system can be employed without departing from the scope of the invention, such as snaps, buttons, belts, straps and the like.

We claim:

1. An orthopedic support comprising:
 a main body having an upper surface, a bottom surface, a first end and a second end, and a top cover assembly secured to the upper surface of the main body at about the first end, the top cover assembly securing a buckle protector and a buckle loop to the upper surface of the main body wherein the buckle protector is positioned between the upper surface of the main body and the buckle loop.

2. The orthopedic support of claim 1, wherein the top cover assembly includes a material piece secured to the upper surface of the main body and the material piece secures the buckle protector and buckle loop to the upper surface of the main body.

3. The orthopedic support of claim 2, further comprising a tendon pad having a pad base and a raised portion projecting from the pad base, wherein the main body defines an opening and wherein the tendon pad is inserted into the opening so that the raised portion projects outwardly from the bottom surface and through the opening.

4. The orthopedic support of claim 3, wherein the material piece of the top cover assembly extends over the opening and secures the tendon pad therein.

5. The orthopedic support of claim 4, wherein the material piece folds over on itself to define an inner opening in which is secured the buckle protector and the buckle loop.

6. The orthopedic support of claim 1, wherein a free end of the buckle protector extends past a free end of the buckle loop.

7. The orthopedic support of claim 6, wherein the free end of the buckle protector falls short of a free edge of the first end.

8. The orthopedic support of claim 7, wherein the free end of the buckle protector is curved.

9. The orthopedic support of claim 8, wherein the buckle protector is substantially a trapezoid with the curved free end.

10. The orthopedic support of claim 9, wherein the buckle protector is made of a substantially rigid material.

11. The orthopedic support of claim 10, wherein the buckle loop has a substantially rectangular shape.

12. The orthopedic support of claim 1, wherein the first end has an enlarged end.

13. The orthopedic support of claim 12, wherein the first end defines a neck positioned subjacent the enlarged end.

14. The orthopedic support of claim 13, wherein a free end of the buckle protector extends past a free end of the buckle loop.

15. The orthopedic support of claim 14, wherein the buckle protector and the buckle loop extend from the neck and toward a free edge of the first end.

* * * * *